(12) United States Patent
de Gromoboy Dabrowicki et al.

(10) Patent No.: US 12,082,618 B2
(45) Date of Patent: Sep. 10, 2024

(54) CARTRIDGES FOR VAPORIZER DEVICES

(71) Applicant: JUUL Labs, Inc., San Francisco, CA (US)

(72) Inventors: Joshua A. de Gromoboy Dabrowicki, Cambridge (GB); Esteban Leon Duque, Berkeley, CA (US); Christopher James Rosser, Cambridge (GB); Andrew J. Stratton, Royston (GB)

(73) Assignee: JUUL Labs, Inc., Washington, DC (US)

( * ) Notice: Subject to any disclaimer, the term of this patent is extended or adjusted under 35 U.S.C. 154(b) by 623 days.

(21) Appl. No.: 17/347,993

(22) Filed: Jun. 15, 2021

(65) Prior Publication Data

US 2021/0307401 A1    Oct. 7, 2021

Related U.S. Application Data

(63) Continuation of application No. PCT/US2019/069118, filed on Dec. 31, 2019.
(Continued)

(51) Int. Cl.
*A24F 40/485* (2020.01)
*A24F 40/10* (2020.01)
*A24F 40/42* (2020.01)

(52) U.S. Cl.
CPC ............ *A24F 40/485* (2020.01); *A24F 40/10* (2020.01); *A24F 40/42* (2020.01)

(58) Field of Classification Search
CPC ......... A24F 40/485; A24F 40/10; A24F 40/42
See application file for complete search history.

(56) References Cited

U.S. PATENT DOCUMENTS

| 4,735,217 A | 4/1988 | Gerth et al. |
| 4,947,874 A | 8/1990 | Brooks et al. |

(Continued)

FOREIGN PATENT DOCUMENTS

| CA | 2883143 C | 7/2017 |
| CN | 102917744 A | 2/2013 |

(Continued)

*Primary Examiner* — Thanh Tam T Le
(74) *Attorney, Agent, or Firm* — Mintz, Levin, Cohn, Ferris, Glovsky and Popeo, P.C.

(57) ABSTRACT

Cartridges for vaporizer devices are provided. In one exemplary embodiment, a cartridge can include a reservoir housing that includes a reservoir chamber configured to contain a vaporizable material and first and second orifices each in fluid communication with the reservoir chamber. The first orifice is configured to allow at least a portion of the vaporizable material to be withdrawn from the reservoir chamber in response to generation of a first pressure differential across the first orifice that exceeds a first predetermined threshold pressure differential. The second orifice is configured to allow a portion of ambient air that is outside the reservoir housing to enter the reservoir chamber in response to generation of a second pressure differential across the second orifice that exceeds a second predetermined threshold pressure differential during the withdrawal of the vaporizable material from the reservoir chamber. Vaporizer devices and methods are also provided.

19 Claims, 6 Drawing Sheets

Related U.S. Application Data

(60) Provisional application No. 62/786,876, filed on Dec. 31, 2018, provisional application No. 62/818,977, filed on Mar. 15, 2019.

(56) References Cited

U.S. PATENT DOCUMENTS

| | | |
|---|---|---|
| 4,947,875 A | 8/1990 | Brooks et al. |
| 5,646,666 A | 7/1997 | Cowger et al. |
| 5,979,548 A | 11/1999 | Rhodes et al. |
| 6,155,268 A | 12/2000 | Takeuchi |
| 6,196,218 B1 | 3/2001 | Voges |
| 6,234,167 B1 | 5/2001 | Cox et al. |
| 6,314,957 B1 | 11/2001 | Boissin et al. |
| 6,501,052 B2 | 12/2002 | Cox et al. |
| 6,766,220 B2 | 7/2004 | McRae et al. |
| 7,167,776 B2 | 1/2007 | Maharajh et al. |
| 7,802,569 B2 | 9/2010 | Yeates et al. |
| 7,913,686 B2 | 3/2011 | Hughes et al. |
| 7,913,688 B2 | 3/2011 | Cross et al. |
| 8,079,361 B2 | 12/2011 | Schuler et al. |
| 8,205,622 B2 * | 6/2012 | Pan .................. A24F 40/51 131/273 |
| 8,485,180 B2 | 7/2013 | Smutney et al. |
| 8,528,569 B1 | 9/2013 | Newton |
| 8,833,364 B2 | 9/2014 | Buchberger |
| 8,851,083 B2 * | 10/2014 | Oglesby .............. A61M 11/042 131/271 |
| 9,247,773 B2 | 2/2016 | Memari et al. |
| 9,302,800 B2 | 4/2016 | Holmes et al. |
| 9,351,522 B2 | 5/2016 | Safari |
| 9,399,110 B2 | 7/2016 | Goodman et al. |
| 9,427,022 B2 | 8/2016 | Levin et al. |
| 9,462,832 B2 | 10/2016 | Lord et al. |
| 9,510,623 B2 | 12/2016 | Tucker et al. |
| 9,642,397 B2 | 5/2017 | Dai et al. |
| 9,648,908 B1 | 5/2017 | Rinehart et al. |
| 9,668,522 B2 | 6/2017 | Memari et al. |
| 9,675,118 B2 | 6/2017 | Chen |
| 9,681,688 B1 | 6/2017 | Rinehart et al. |
| 9,714,878 B2 * | 7/2017 | Powers .................. G01L 7/08 |
| 9,763,478 B2 | 9/2017 | Cameron et al. |
| 9,770,055 B2 | 9/2017 | Cameron et al. |
| 9,802,011 B2 | 10/2017 | Davidson et al. |
| 9,839,238 B2 * | 12/2017 | Worm ................. A24F 40/40 |
| 9,877,519 B2 | 1/2018 | Xiang |
| 9,888,723 B2 | 2/2018 | Cameron et al. |
| 10,034,988 B2 | 7/2018 | Wensley et al. |
| 10,058,128 B2 | 8/2018 | Cameron et al. |
| 10,058,129 B2 | 8/2018 | Monsees et al. |
| 10,085,486 B2 | 10/2018 | Cameron |
| 10,130,123 B2 * | 11/2018 | Hatton ................ H05B 1/0244 |
| 10,131,532 B2 | 11/2018 | Murison et al. |
| 10,188,148 B2 | 1/2019 | Althorpe et al. |
| 10,272,170 B2 * | 4/2019 | Dubief ................ A24F 40/485 |
| 10,278,421 B2 | 5/2019 | Lord |
| 10,292,427 B2 | 5/2019 | Cameron et al. |
| 10,334,884 B2 * | 7/2019 | Rogan ................... H05B 6/108 |
| 10,357,060 B2 | 7/2019 | Rostami et al. |
| 10,375,990 B2 | 8/2019 | Lord |
| 10,405,579 B2 | 9/2019 | Collett et al. |
| 10,412,996 B2 | 9/2019 | Bright et al. |
| 10,492,528 B2 * | 12/2019 | Gavrielov ............ H05B 1/0297 |
| 10,772,357 B2 * | 9/2020 | Saygili ................. A24F 40/42 |
| 11,154,669 B2 * | 10/2021 | Bowen ................. A24F 40/50 |
| 11,273,428 B2 * | 3/2022 | Lindars ............... A61M 11/041 |
| 11,278,058 B2 * | 3/2022 | Atkins .................. A24F 40/44 |
| 11,553,734 B2 * | 1/2023 | Rosser ................. A24F 40/48 |
| 11,612,186 B2 * | 3/2023 | Watanabe ........... A24F 40/485 131/329 |
| 11,647,790 B2 * | 5/2023 | Habicht ............... A24F 40/42 131/329 |
| 11,771,850 B2 * | 10/2023 | Habicht ............... A24F 40/485 131/328 |
| 2003/0015045 A1 | 1/2003 | Yoshida et al. |
| 2003/0063901 A1 | 4/2003 | Gu et al. |
| 2004/0182855 A1 | 9/2004 | Centanni |
| 2005/0034723 A1 | 2/2005 | Bennett et al. |
| 2005/0268911 A1 | 12/2005 | Cross et al. |
| 2006/0196505 A1 | 9/2006 | Izuchukwu |
| 2007/0169773 A1 | 7/2007 | Rock |
| 2008/0216828 A1 | 9/2008 | Wensley et al. |
| 2009/0324206 A1 | 12/2009 | Young et al. |
| 2010/0181387 A1 | 7/2010 | Zaffaroni et al. |
| 2012/0199146 A1 | 8/2012 | Marangos |
| 2013/0019862 A1 | 1/2013 | Yamada et al. |
| 2013/0327327 A1 | 12/2013 | Edwards et al. |
| 2014/0041658 A1 | 2/2014 | Goodman et al. |
| 2014/0150810 A1 | 6/2014 | Hon |
| 2014/0158129 A1 | 6/2014 | Pratt et al. |
| 2014/0190496 A1 | 7/2014 | Wensley et al. |
| 2015/0047661 A1 | 2/2015 | Blackley et al. |
| 2015/0053220 A1 | 2/2015 | Levy et al. |
| 2015/0114504 A1 | 4/2015 | Cecka et al. |
| 2015/0208731 A1 | 7/2015 | Malamud et al. |
| 2015/0216232 A1 | 8/2015 | Bless et al. |
| 2015/0216236 A1 | 8/2015 | Bless et al. |
| 2015/0216237 A1 | 8/2015 | Wensley et al. |
| 2015/0223522 A1 | 8/2015 | Ampolini et al. |
| 2015/0245654 A1 | 9/2015 | Memari et al. |
| 2015/0245655 A1 | 9/2015 | Memari et al. |
| 2015/0245657 A1 | 9/2015 | Memari et al. |
| 2015/0245662 A1 | 9/2015 | Memari et al. |
| 2015/0245665 A1 | 9/2015 | Memari et al. |
| 2015/0245666 A1 | 9/2015 | Memari et al. |
| 2015/0245667 A1 | 9/2015 | Memari et al. |
| 2015/0245668 A1 | 9/2015 | Memari et al. |
| 2015/0257447 A1 | 9/2015 | Sullivan |
| 2015/0282524 A1 | 10/2015 | Elhalwani |
| 2015/0289565 A1 | 10/2015 | Cadieux et al. |
| 2016/0058073 A1 | 3/2016 | Chen |
| 2016/0128387 A1 | 5/2016 | Chen |
| 2016/0129205 A1 | 5/2016 | Shahaf et al. |
| 2016/0150824 A1 | 6/2016 | Memari et al. |
| 2016/0166564 A1 | 6/2016 | Myers et al. |
| 2016/0206000 A1 | 7/2016 | Lord et al. |
| 2016/0262453 A1 | 9/2016 | Ampolini et al. |
| 2016/0270446 A1 | 9/2016 | Shenkal et al. |
| 2016/0324217 A1 | 11/2016 | Cameron |
| 2016/0325055 A1 | 11/2016 | Cameron |
| 2016/0331022 A1 | 11/2016 | Cameron |
| 2016/0331023 A1 | 11/2016 | Cameron |
| 2016/0331024 A1 | 11/2016 | Cameron |
| 2016/0331025 A1 | 11/2016 | Cameron |
| 2016/0331026 A1 | 11/2016 | Cameron |
| 2016/0331027 A1 | 11/2016 | Cameron |
| 2016/0331028 A1 | 11/2016 | Xu |
| 2016/0331034 A1 | 11/2016 | Cameron |
| 2016/0331859 A1 | 11/2016 | Cameron |
| 2016/0331913 A1 | 11/2016 | Bourque |
| 2016/0334119 A1 | 11/2016 | Cameron |
| 2016/0334847 A1 | 11/2016 | Cameron |
| 2016/0337141 A1 | 11/2016 | Cameron |
| 2016/0337362 A1 | 11/2016 | Cameron |
| 2016/0337444 A1 | 11/2016 | Cameron |
| 2016/0356751 A1 | 12/2016 | Blackley |
| 2016/0363570 A1 | 12/2016 | Blackley |
| 2016/0363917 A1 | 12/2016 | Blackley |
| 2016/0367925 A1 | 12/2016 | Blackley |
| 2016/0370335 A1 | 12/2016 | Blackley |
| 2017/0018000 A1 | 1/2017 | Cameron |
| 2017/0020188 A1 | 1/2017 | Cameron |
| 2017/0020195 A1 | 1/2017 | Cameron |
| 2017/0020196 A1 | 1/2017 | Cameron |
| 2017/0020197 A1 | 1/2017 | Cameron |
| 2017/0027229 A1 | 2/2017 | Cameron |
| 2017/0042230 A1 | 2/2017 | Cameron |
| 2017/0042231 A1 | 2/2017 | Cameron |
| 2017/0042247 A1 | 2/2017 | Xiang |
| 2017/0042248 A1 | 2/2017 | Xiang |
| 2017/0045994 A1 | 2/2017 | Murison et al. |
| 2017/0046357 A1 | 2/2017 | Cameron |
| 2017/0046738 A1 | 2/2017 | Cameron |
| 2017/0055588 A1 | 3/2017 | Cameron |

(56) References Cited

U.S. PATENT DOCUMENTS

| | | |
|---|---|---|
| 2017/0071249 A1 | 3/2017 | Ampolini et al. |
| 2017/0086496 A1 | 3/2017 | Cameron |
| 2017/0086497 A1 | 3/2017 | Cameron |
| 2017/0086503 A1 | 3/2017 | Cameron |
| 2017/0086504 A1 | 3/2017 | Cameron |
| 2017/0091853 A1 | 3/2017 | Cameron |
| 2017/0092106 A1 | 3/2017 | Cameron |
| 2017/0093960 A1 | 3/2017 | Cameron |
| 2017/0093981 A1 | 3/2017 | Cameron |
| 2017/0119058 A1 | 5/2017 | Cameron |
| 2017/0135399 A1 | 5/2017 | Gavrielov et al. |
| 2017/0135407 A1 | 5/2017 | Cameron |
| 2017/0135408 A1 | 5/2017 | Cameron |
| 2017/0135409 A1 | 5/2017 | Cameron |
| 2017/0135411 A1 | 5/2017 | Cameron |
| 2017/0135412 A1 | 5/2017 | Cameron |
| 2017/0136193 A1 | 5/2017 | Cameron |
| 2017/0136194 A1 | 5/2017 | Cameron |
| 2017/0136196 A1 | 5/2017 | Davidson et al. |
| 2017/0136301 A1 | 5/2017 | Cameron |
| 2017/0170439 A1 | 6/2017 | Jarvis et al. |
| 2017/0172210 A1 | 6/2017 | Bright et al. |
| 2017/0181471 A1 | 6/2017 | Phillips et al. |
| 2017/0181474 A1 | 6/2017 | Cameron et al. |
| 2017/0181475 A1 | 6/2017 | Cameron |
| 2017/0185364 A1 | 6/2017 | Cameron |
| 2017/0208863 A1 | 7/2017 | Phillips et al. |
| 2017/0245547 A1 | 8/2017 | Lipowicz |
| 2017/0258138 A1 | 9/2017 | Rostami et al. |
| 2017/0258140 A1 | 9/2017 | Rostami et al. |
| 2017/0259170 A1 | 9/2017 | Bowen et al. |
| 2017/0303590 A1 | 10/2017 | Cameron et al. |
| 2017/0303593 A1 | 10/2017 | Cameron et al. |
| 2017/0303594 A1 | 10/2017 | Cameron et al. |
| 2017/0309091 A1 | 10/2017 | Cameron et al. |
| 2017/0332702 A1 | 11/2017 | Cameron et al. |
| 2017/0354183 A1 | 12/2017 | Liu |
| 2017/0360093 A1 | 12/2017 | Fernando |
| 2017/0367407 A1 | 12/2017 | Althorpe et al. |
| 2018/0027883 A1 | 2/2018 | Zuber et al. |
| 2018/0093051 A1 | 4/2018 | Stenzler et al. |
| 2018/0116292 A1 | 5/2018 | Atkins et al. |
| 2018/0146715 A1 | 5/2018 | Takeuchi et al. |
| 2018/0184722 A1 | 7/2018 | Murison et al. |
| 2018/0199627 A1 | 7/2018 | Bowen et al. |
| 2018/0296777 A1 | 10/2018 | Terry et al. |
| 2019/0046745 A1 | 2/2019 | Nettenstrom et al. |
| 2019/0104767 A1 | 4/2019 | Hatton et al. |
| 2019/0159519 A1 | 5/2019 | Bowen et al. |
| 2019/0166913 A1 | 6/2019 | Trzecieski |
| 2019/0246693 A1 | 8/2019 | Nettenstrom et al. |
| 2019/0373953 A1 | 12/2019 | Atkins et al. |
| 2020/0000146 A1 | 1/2020 | Anderson et al. |
| 2020/0022417 A1 | 1/2020 | Atkins et al. |
| 2020/0077707 A1 | 3/2020 | Alston et al. |
| 2020/0113245 A1 | 4/2020 | Rosser et al. |
| 2020/0114094 A1 | 4/2020 | Atkins et al. |
| 2020/0128874 A1 | 4/2020 | Atkins et al. |
| 2020/0138113 A1 | 5/2020 | Rosser et al. |
| 2020/0329763 A1* | 10/2020 | Kerr .................. A61M 15/0066 |
| 2021/0307392 A1* | 10/2021 | Rosser .................. A24F 40/10 |
| 2021/0352960 A1* | 11/2021 | Simrell ............. A61M 15/0021 |
| 2022/0046994 A1* | 2/2022 | Woods .................. A24F 40/485 |

FOREIGN PATENT DOCUMENTS

| | | |
|---|---|---|
| CN | 103501847 A | 1/2014 |
| CN | 104544565 A | 4/2015 |
| CN | 205390306 U | 7/2016 |
| CN | 206390296 U | 8/2017 |
| CN | 107809918 A | 3/2018 |
| CN | 108289510 A | 7/2018 |
| CN | 108606366 A | 10/2018 |
| CN | 108778006 A | 11/2018 |
| CN | 105899094 B | 5/2019 |
| CN | 105476069 B | 6/2019 |
| DE | 102017123869 B4 | 5/2019 |
| EP | 0358002 A2 | 3/1990 |
| EP | 0358114 A2 | 3/1990 |
| EP | 3220987 A1 | 9/2017 |
| EP | 3423058 A1 | 1/2019 |
| EP | 3220987 B1 | 5/2019 |
| EP | 3261465 B1 | 6/2019 |
| GB | 2522727 B | 1/2017 |
| JP | 2009505649 A | 2/2009 |
| JP | 2009131367 A | 6/2009 |
| KR | 100679751 B1 | 2/2007 |
| KR | 100971178 B1 | 7/2010 |
| KR | 101430282 B1 | 8/2014 |
| KR | 101724522 B1 | 4/2017 |
| WO | WO 9501137 A1 | 1/1995 |
| WO | WO 2008077271 A1 | 7/2008 |
| WO | WO 2010145805 A1 | 12/2010 |
| WO | WO 2012026963 A2 | 3/2012 |
| WO | WO 2015066136 A1 | 5/2015 |
| WO | WO 2015148649 A2 | 10/2015 |
| WO | WO 2016019550 A1 | 2/2016 |
| WO | WO 2016079151 A1 | 5/2016 |
| WO | WO 2016079533 A1 | 5/2016 |
| WO | WO 2016090602 A1 | 6/2016 |
| WO | WO 2016119248 A1 | 8/2016 |
| WO | WO 2016127361 A1 | 8/2016 |
| WO | WO 2016179376 A1 | 11/2016 |
| WO | WO 2016187110 A1 | 11/2016 |
| WO | WO 2017036819 A1 | 3/2017 |
| WO | WO 2017054424 A1 | 4/2017 |
| WO | WO 2017064051 A1 | 4/2017 |
| WO | WO 2017064323 A1 | 4/2017 |
| WO | WO 2017072239 A1 | 5/2017 |
| WO | WO 2017072277 A1 | 5/2017 |
| WO | WO 2017072284 A1 | 5/2017 |
| WO | WO 2017085240 A1 | 5/2017 |
| WO | WO 2017108268 A1 | 6/2017 |
| WO | WO 2017143865 A1 | 8/2017 |
| WO | WO 2017163046 A1 | 9/2017 |
| WO | WO 2017163051 A1 | 9/2017 |
| WO | WO 2019173923 A1 | 9/2019 |
| WO | WO 2019232086 A1 | 12/2019 |
| WO | WO 2020006305 A1 | 1/2020 |

\* cited by examiner

CARTRIDGES FOR VAPORIZER DEVICES

CROSS-REFERENCE TO RELATED APPLICATIONS

This application is a continuation application, filed under 35 U.S.C. § 120, of PCT International Patent Application No. PCT/US19/69118 with an International Filing Date of Dec. 31, 2019, and entitled "Cartridges For Vaporizer Devices," which claims priority to U.S. Provisional Patent Application Nos. 62/786,876 and 62/818,977, filed on Dec. 31, 2018 and Mar. 15, 2019, respectively, and entitled "Cartridges For Vaporizer Devices," the disclosures of all of which are incorporated herein by reference in their entirety.

TECHNICAL FIELD

The subject matter described herein relates to vaporizer devices, including a disposable vaporizer cartridge.

BACKGROUND

Vaporizer devices, which can also be referred to as vaporizers, electronic vaporizer devices, or e-vaporizer devices, can be used for delivery of an aerosol (for example, a vapor-phase and/or condensed-phase material suspended in a stationary or moving mass of air or some other gas carrier) containing one or more active ingredients by inhalation of the aerosol by a user of the vaporizing device. For example, electronic nicotine delivery systems (ENDS) include a class of vaporizer devices that are battery powered and that can be used to simulate the experience of smoking, but without burning of tobacco or other substances. Vaporizer devices are gaining increasing popularity both for prescriptive medical use, in delivering medicaments, and for consumption of tobacco, nicotine, and other plant-based materials. Vaporizer devices can be portable, self-contained, and/or convenient for use.

In use of a vaporizer device, the user inhales an aerosol, colloquially referred to as "vapor," which can be generated by a heating element that vaporizes (e.g., causes a liquid or solid to at least partially transition to the gas phase) a vaporizable material, which can be liquid, a solution, a solid, a paste, a wax, and/or any other form compatible for use with a specific vaporizer device. The vaporizable material used with a vaporizer device can be provided within a vaporizer cartridge (for example, a separable part of the vaporizer device that contains vaporizable material) that includes an outlet (for example, a mouthpiece) for inhalation of the aerosol by a user.

To receive the inhalable aerosol generated by a vaporizer device, a user may, in certain examples, activate the vaporizer device by taking a puff, by pressing a button, and/or by some other approach. A puff as used herein can refer to inhalation by the user in a manner that causes a volume of air to be drawn into the vaporizer device such that the inhalable aerosol is generated by a combination of the vaporized vaporizable material with the volume of air.

Vaporizer devices can be controlled by one or more controllers, electronic circuits (for example, sensors, heating elements), and/or the like on the vaporizer device. Vaporizer devices can also wirelessly communicate with an external controller for example, a computing device such as a smartphone).

An approach by which a vaporizer device generates an inhalable aerosol from a vaporizable material involves heating the vaporizable material in a vaporization chamber (e.g., a heater chamber) to cause the vaporizable material to be converted to the gas (or vapor) phase. A vaporization chamber can refer to an area or volume in the vaporizer device within which a heat source (for example, a conductive, convective, and/or radiative heat source) causes heating of a vaporizable material to produce a mixture of air and vaporized material to form a vapor for inhalation of the vaporizable material by a user of the vaporizer device.

In some implementations, the vaporizable material can be drawn out of a reservoir and into the vaporization chamber via a wicking element (e.g., a wick). Drawing of the vaporizable material into the vaporization chamber can be at least partially due to capillary action provided by the wicking element as the wicking element pulls the vaporizable material along the wicking element in the direction of the vaporization chamber. However, as vaporizable material is drawn out of the reservoir chamber, the pressure inside the reservoir chamber is reduced, thereby creating a vacuum and acting against the capillary action. This can reduce the effectiveness of the wick to draw the vaporizable material into the vaporization chamber. Further, the wicking element degrades over time, which can adversely affect device performance, and ultimately renders the device unsafe to use. As a result, the wicking element, and in some instances the entire device, must be replaced. In other vaporizer device embodiments, the vaporizable material can be drawn out of a reservoir chamber via an electric pump. However, the use of electric pumps typically requires significant amounts of power to operate.

Accordingly, vaporizer devices and/or vaporizer cartridges that address one or more of these issues are desired.

SUMMARY

Aspects of the current subject matter relate to cartridges, vaporizer devices, and methods for triggering flow of a vaporizable material from a reservoir chamber in response to a pressure differential that is created by an inhalation vacuum that exceeds a predetermined threshold. Accordingly, a user's puff can be used to control the flow of the vaporizable material from the reservoir chamber for vaporization.

In some variations, one or more of the following features may optionally be included in any feasible combination.

Cartridges for vaporizer devices are provided. In one exemplary embodiment, a cartridge is provided and includes a reservoir housing that includes a reservoir chamber configured to contain a vaporizable material, a first orifice extending through a first wall of the reservoir housing and in fluid communication with the reservoir chamber, and a second orifice extending through a second wall of the reservoir housing and in fluid communication with the reservoir chamber. The first orifice is configured to allow at least a portion of the vaporizable material to be withdrawn from the reservoir chamber in response to generation of a first pressure differential across the first orifice that exceeds a first predetermined threshold pressure differential. The second orifice is configured to allow a portion of ambient air that is outside the reservoir housing to enter the reservoir chamber in response to generation of a second pressure differential across the second orifice that exceeds a second predetermined threshold pressure differential during the withdrawal of the vaporizable material from the reservoir chamber.

In some embodiments, the first pressure differential can exceed the first predetermined threshold pressure differential in response to the first orifice being exposed to an inhalation vacuum that exceeds a predetermined threshold inhalation vacuum.

In some embodiments, the vaporizable material can be maintained within the reservoir chamber until the first pressure differential exceeds the first predetermined threshold pressure differential.

In some embodiments, the first orifice can have a first diameter and the second orifice can have a second diameter that is greater than the first diameter.

In some embodiments, the first orifice can be configured to control a flow rate of the vaporizable material being withdrawn from the reservoir chamber along the first orifice. In other embodiments, the second orifice can be configured to control a flow rate of the ambient air being drawn along the second orifice into the reservoir chamber.

In some embodiments, the first orifice can be configured to direct the vaporizable material being withdrawn from the reservoir chamber along the first orifice to a heating element for vaporization.

In some embodiments, the cartridge can include a third orifice that extends through the first wall of the reservoir housing and in fluid communication with reservoir chamber. The third orifice can be configured to allow at least another portion of the vaporizable material to be withdrawn from the reservoir chamber in response to generation of a third pressure differential across the third orifice that exceeds a third predetermined threshold pressure differential.

In some embodiments, the cartridge can include a third orifice that extends through the second wall of the reservoir housing and in fluid communication with reservoir chamber. The third orifice can be configured to allow at least another portion of ambient air outside of the reservoir housing to enter the reservoir chamber in response to generation of a third pressure differential across the third orifice that exceeds a third predetermined threshold pressure differential during the withdrawal of the vaporizable material from the reservoir chamber.

In some embodiments, the cartridge can include a first tubular member that can extend through the first wall of the reservoir housing and into the reservoir chamber. The first tubular member can define the first orifice.

In some embodiments, the cartridge can include a second tubular member that can extend through the second wall of the reservoir housing and into the reservoir chamber. The second tubular member can define the second orifice.

In another exemplary embodiment, a cartridge is provided and can include a reservoir housing that includes a reservoir chamber configured to contain a vaporizable material, and first and second tubular members that are each in fluid communication with and at least partially extending into the reservoir chamber. The first tubular member is configured to withdraw at least a portion of the vaporizable material from the reservoir chamber in response to being exposed to an inhalation vacuum that exceeds a predetermined threshold inhalation vacuum. The second tubular member is configured to concurrently allow a portion of ambient air outside of the reservoir housing to pass therethrough and into the reservoir chamber while the inhalation vacuum is above the predetermined threshold inhalation vacuum. In one embodiment, the first tubular member can have a first inner diameter and the second tubular member can have a second inner diameter that is greater than the first inner diameter.

In some embodiments, the cartridge can include a third tubular member that is in fluid communication with and at least partially extending into the reservoir chamber. In one embodiment, the third tubular member can be configured to withdraw at least another portion of the vaporizable material from the reservoir chamber in response to being exposed to the inhalation vacuum that exceeds the predetermined threshold inhalation vacuum. In another embodiment, the third tubular member can be configured to concurrently allow at least another portion of ambient air outside the reservoir housing to pass therethrough and into the reservoir chamber while the inhalation vacuum is above the predetermined threshold inhalation vacuum.

Vaporizer devices are also provided. In one exemplary embodiment, a vaporizer device is provided and includes a vaporizer body and a cartridge that is selectively coupled to and removable from the vaporizer body. The vaporizer body includes a heating element disposed therein. The cartridge includes a reservoir housing that includes a reservoir chamber configured to contain a vaporizable material, a first orifice extending through a first wall of the reservoir housing and in fluid communication with the reservoir chamber, and a second orifice extending through a second wall of the reservoir housing and in fluid communication with the reservoir chamber. The first orifice is configured to allow at least a portion of the vaporizable material to be withdrawn from the reservoir chamber in response to generation of a first pressure differential across the first orifice that exceeds a first predetermined threshold pressure differential. The second orifice is configured to allow a portion of ambient air that is outside the reservoir housing to enter the reservoir chamber in response to generation of a second pressure differential across the second orifice that exceeds a second predetermined threshold pressure differential during the withdrawal of the vaporizable material from the reservoir chamber. The first orifice is in communication with the heating element for vaporization of the withdrawn vaporizable material into a vaporized material.

In some embodiments, the heating element can be in the form of a mesh structure. In other embodiments, the heating element can be in the form of a plate that includes at least one groove that is configured to receive the withdrawn vaporizable material. In yet other embodiments, the heating element can include at least one tine.

In some embodiments, the vaporizer body can include a first airflow path and the cartridge can include a second airflow path that is in fluid communication with the first airflow path.

In some embodiments, the vaporizer body can include at least one inlet that is configured to substantially allow airflow to pass into the vaporizer body. The at least one inlet can be in fluid communication with the first airflow path.

Methods are also provided. In one exemplary embodiment, the method includes generating a vacuum within a vaporizer device that exceeds a predetermined threshold vacuum, the vaporizer device including a vaporizer body, a cartridge coupled to the vaporizer body, and a vaporization chamber, the cartridge including a reservoir housing, a reservoir chamber residing within the reservoir housing and configured to hold a vaporizable material, and a plurality of orifices in fluid communication with the reservoir chamber, drawing, in response to the vacuum being applied to a first orifice of the plurality of orifices, a portion of the vaporizable material along the first orifice from the reservoir chamber and into the vaporization chamber thereby decreasing an internal pressure of the reservoir chamber, and drawing a portion of ambient air outside of the reservoir housing along a second orifice of the plurality of orifices into the reservoir chamber to increase the internal pressure of the reservoir chamber during the withdrawal of the vaporization material from the reservoir chamber.

In some embodiments, the first orifice can be defined by a first tubular member that extends from an exterior surface of a first wall of the reservoir housing and into the reservoir chamber, and the second orifice can be defined by a second tubular member that extends from an exterior surface of a second wall of the reservoir housing and into the reservoir chamber.

The details of one or more variations of the subject matter described herein are set forth in the accompanying drawings and the description below. Other features and advantages of the subject matter described herein will be apparent from the description and drawings, and from the claims. The claims that follow this disclosure are intended to define the scope of the protected subject matter.

BRIEF DESCRIPTION OF THE DRAWINGS

The accompanying drawings, which are incorporated into and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
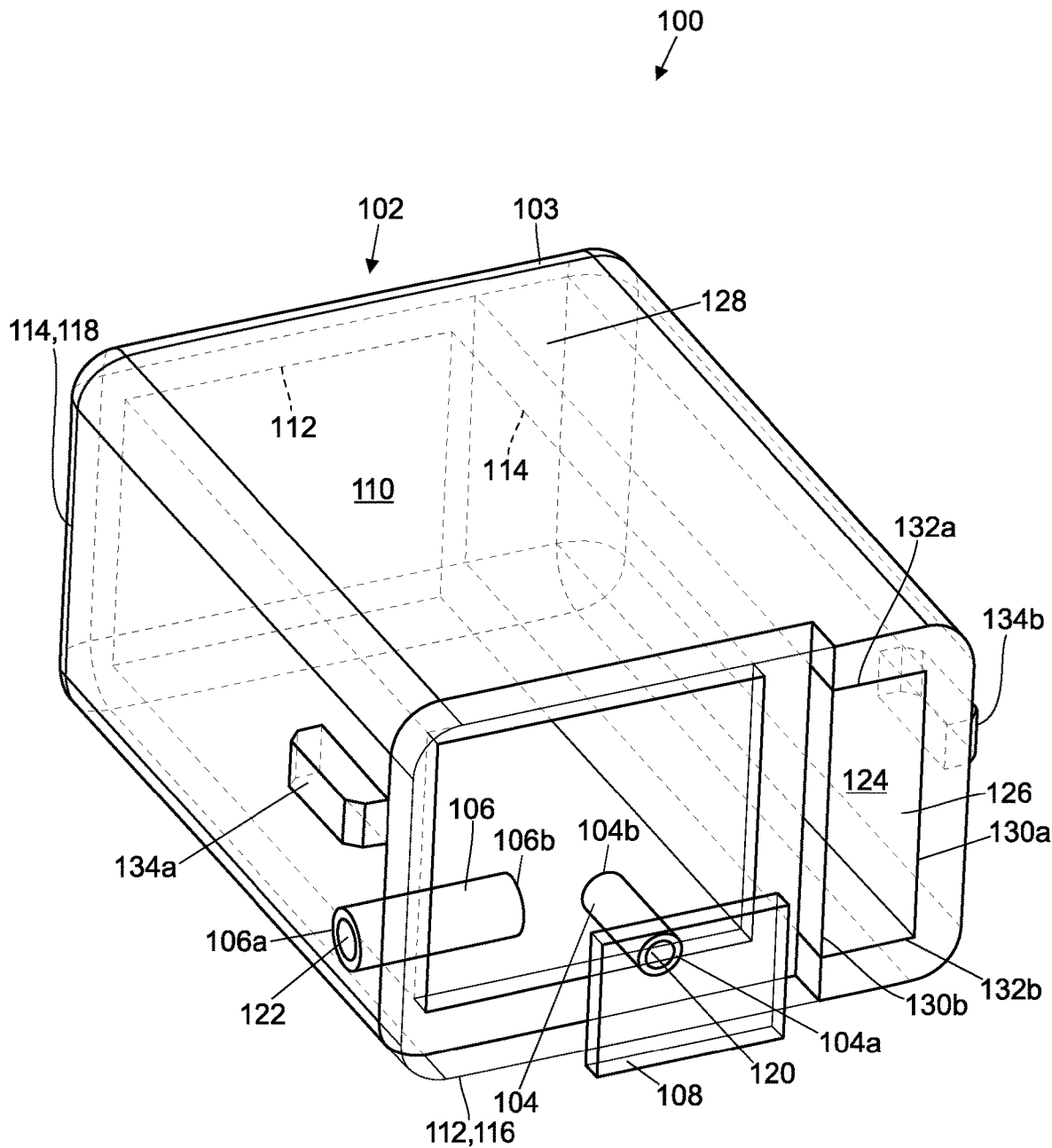
FIG. 1 is a partially transparent, bottom-up isometric view of an embodiment of a vaporizer cartridge in communication with a heating element.

Implementations of the current subject matter include methods, apparatuses, articles of manufacture, and systems relating to vaporization of one or more materials for inhalation by a user. Example implementations include vaporizer devices and systems including vaporizer devices. The term "vaporizer device" as used in the following description and claims refers to any of a self-contained apparatus, an apparatus that includes two or more separable parts (for example, a vaporizer body that includes a battery and other hardware, and a vaporizer cartridge that includes a vaporizable material), and/or the like. A "vaporizer system," as used herein, can include one or more components, such as a vaporizer device. Examples of vaporizer devices consistent with implementations of the current subject matter include electronic vaporizers, electronic nicotine delivery systems (ENDS), and/or the like. In general, such vaporizer devices are hand-held devices that heat (such as by convection, conduction, radiation, and/or some combination thereof) a vaporizable material to provide an inhalable dose of the material.

The vaporizable material used with a vaporizer device can be provided within a vaporizer cartridge (for example, a part of the vaporizer device that contains the vaporizable material in a reservoir or other container) which can be refillable when empty, or disposable such that a new vaporizer cartridge containing additional vaporizable material of a same or different type can be used). A vaporizer device can be a cartridge-using vaporizer device, a cartridge-less vaporizer device, or a multi-use vaporizer device capable of use with or without a cartridge. For example, a vaporizer device can include a heating chamber (for example, an oven or other region in which material is heated by a heating element) configured to receive a vaporizable material directly into the heating chamber, and/or a reservoir or the like for containing the vaporizable material.

In some implementations, a vaporizer device can be configured for use with a liquid vaporizable material. For example, the liquid vaporizable material may include a carrier solution in which an active and/or inactive ingredient(s) are suspended or held in solution. Alternatively, the liquid vaporizable material may be a liquid form of the vaporizable material itself. The liquid vaporizable material can be capable of being completely vaporized. Alternatively, at least a portion of the liquid vaporizable material can remain after all of the material suitable for inhalation has been vaporized.

As mentioned above, existing vaporizer devices or vaporizer cartridges can include a wicking element that is configured to withdraw vaporizable material from a reservoir chamber such that the vaporizable material may be subsequently vaporized (e.g., by exposing the withdrawn vaporizable material to heat provided by a heating element). In such instances, however, the capillary action of the wicking element can be compromised (e.g., by the creation of a vacuum within the reservoir chamber, degradation of the wicking element, and the like). As a result, it can be difficult to modulate or control the withdrawal of the vaporizable material. Alternatively, an electric pump can be used to withdraw the vaporizable material. However, due to the amount of power needed to actuate the electric pump, such configurations can be expensive. Various features and devices are described below that improve upon or overcome these foregoing issues.

The vaporizer cartridges described herein allow for controlled delivery of vaporizable material from a reservoir chamber in response to the application of an inhalation vacuum that exceeds a predetermined threshold inhalation vacuum. That is, the vaporizer cartridges include a breath-modulated mechanism that controls delivery of the vaporizable material. The inhalation vacuum is generated in association with a suction force provided by a user puffing (e.g., drawing, inhaling, etc.) directly on the vaporizer cartridge itself, or alternatively, on a mouthpiece coupled thereto. Once the inhalation vacuum exceeds the predetermined threshold, the breath-modulated mechanism is actuated to thereby cause vaporizable material to be withdrawn from the reservoir chamber for vaporization. As a result, this eliminates the need to include a wicking element or an electric pump within the vaporizer cartridge for drawing vaporizable material. Further, the withdrawing of the vaporizable material can be substantially achieved without the use of moving parts or electrical contacts within the vaporizer cartridge for electrically coupling the electric pump to a power source.

The vaporizer cartridges described herein generally include a reservoir housing having a reservoir chamber that is configured to contain a vaporizable material, a first orifice that extends through a first wall of the reservoir housing, and a second orifice that extends through a second wall of the reservoir housing. The first and second orifices are each in fluid communication with the reservoir chamber. As discussed in more detail below, the first orifice is configured to allow at least a portion of the vaporizable material to be withdrawn from the reservoir chamber and the second orifice is configured to allow a portion of ambient air that is outside the reservoir housing to enter the reservoir chamber. The withdrawal of the at least a portion vaporizable material from, and the influx of the portion of ambient air into, the reservoir chamber occurs when effective pressure differentials (e.g., pressure differentials that exceed respective predetermined threshold pressure differentials) are created across the first orifice and across the second orifice. These pressure differentials are generated by the application of an inhalation vacuum that exceeds a predetermined threshold inhalation vacuum. For example, at least a portion of vaporizable material may be withdrawn from the reservoir chamber when the inhalation vacuum and the hydrostatic head pressure of the vaporizable material above the first orifice are sufficient to overcome the surface tension of the vaporizable material across the first orifice. It should be noted that the predetermined threshold inhalation vacuum can vary, for example, due to a specific orientation of the vaporizer cartridge and/or environmental factors, such as any type of negative pressure event (e.g., pressure drop inside an airplane cabin).

In some embodiments, the vaporizer body includes a cartridge receptacle that is configured to receive at least a portion of the vaporizer cartridge. In one embodiment, the cartridge receptacle is defined by a sleeve of the vaporizer body.

The reservoir housing can have a variety of configurations. The reservoir housing includes at least one wall that defines the reservoir chamber. In some embodiments, the reservoir housing can have a substantially rectangular configuration. In other embodiments, the reservoir can have any other possible shape.

In some embodiments, the first orifice can be configured to control a flow rate of the vaporizable material being withdrawn from the reservoir chamber along the first orifice. Alternatively, or in addition, the second orifice can be configured to control a flow rate of the ambient air being drawn along the second orifice into the reservoir chamber.

The first and second orifices can have a variety of configurations. In some embodiments, the first and second orifices can each have a substantially circular shape, whereas in other embodiments, the first and second orifices can each have any other possible shape. In one embodiment, the first and second orifices have the same shape relative to each, whereas in another embodiment, the first and second orifices have a different shape relative to each other.

The first and second orifices can each extend from a first end to a second end. In one embodiment, the first and second orifices each extend at least the width of the first and second wall of the reservoir housing, respectively, such that the first end of each orifice is in direct contact with vaporizable material disposed within the reservoir chamber.

The first and second orifices each have a diameter. In one embodiment, the first orifice has a diameter that is less than a diameter of the second orifice. It is contemplated herein that the first and second orifices can have any suitable cross-section.

Prior to the generation of pressure differentials across the first and second orifices in response to an inhalation vacuum, a liquid bubble can form outside of an end of the first orifice that is not in direct contact with vaporizable material disposed within the reservoir chamber. Further, an air bubble can form in the inside of an end of the second orifice that is in direct contact with vaporizable material disposed within the reservoir chamber. That is, the surface tension in the curved liquid-air interfaces allows the reservoir chamber to withstand a given threshold pressure drop. As a result, the vaporizable material can remain therein until an inhalation vacuum is applied that causes a pressure drop that is greater than the given threshold pressure drop (e.g., the application of an inhalation vacuum that exceeds a predetermined threshold inhalation vacuum). As such, the flow rate of the vaporizable material from the reservoir chamber can be dependent at least upon the diameter of the first orifice, and the predetermined threshold inhalation vacuum can be dependent at least upon the diameter of the second orifice.

In use, a user puff's directly on the vaporizer cartridge itself, or alternatively, on a mouthpiece coupled thereto, thereby creating an inhalation vacuum. Once this inhalation vacuum exceeds a predetermined threshold inhalation vacuum, effective pressure differentials are concurrently created across each orifice. As a result, the vaporizable material will begin to travel along the first orifice from the reservoir chamber for vaporization and ambient air will concurrently travel along the second orifice and into the reservoir chamber. That is, once the pressure differentials across each orifice exceed their respective predetermined threshold pressure differentials, the vaporizable material can be withdrawn from, and ambient air can enter, the reservoir chamber. Further, as the inhalation vacuum increases past the predetermined threshold inhalation vacuum, the flow rate of the vaporizable material through the first orifice will increase linearly with pressure difference.

In some embodiments, a regulator valve can be positioned upstream of the first orifice. Once the predetermined threshold inhalation vacuum is exceeded, the flow regulator valve can be configured to produce a substantially consistent pressure drop across the first orifice. Moreover, the flow regulator valve can maintain a consistent pressure drop even during variations in inhalation vacuum during puffing. In this way, the vaporizable material can flow through the first orifice at a substantially constant flow rate over a wide range of inhalation vacuum levels, including at the lowest possible level where flow of vaporization material through the first orifice is permitted.

The flow regulator valve can have a variety of configurations. In some embodiments, the regulating valve can include a resilient material with one or more deformable walls that move to close an inlet into the air flow path that extends through a coupled vaporizer body and vaporizer cartridge as the inhalation vacuum increases.

While the first and second orifices can be positioned at varying distances relative to each other, the distance therebetween can have an effect on hydrostatic head. For example, the first and second orifices can be positioned at a distance relative to each other that minimizes hydrostatic head between them so as to prevent variation in performance relative to orientation of the vaporizer cartridge. In other instances, greater distances between the first and second orifices can result in a hydrostatic head that decreases the predetermined threshold inhalation vacuum, and thus causes variations in performance, when the vaporizer cartridge is in certain orientations.

In some embodiments, the first and/or second orifices are each defined with a respective tubular member. For example, in one embodiment, the first orifice can be defined by a first tubular member that extends through the first wall of the reservoir housing and into the reservoir chamber. Alternatively, or in addition, the second orifice is defined by a second tubular member that extends through the second wall of the reservoir housing and into the reservoir chamber. The first and second tubular members each extend from respective first and second ends and have a length extending therebetween. The first tubular member can have a length that is less than a length of the second tubular member or vice versa.

In some embodiments, the vaporizer cartridge can include additional orifices that function similar to the first or second orifices described above. For example, in one embodiment, a third orifice can extend through the first wall of the reservoir housing and be configured to allow at least another portion of the vaporizable material to be withdrawn from the reservoir chamber in response to generation of a third pressure differential across the third orifice that exceeds a predetermined threshold pressure differential. In another embodiment, the third orifice can extend through the second wall of the reservoir housing configured to allow at least another portion of ambient air outside of the reservoir housing to enter the reservoir chamber in response to generation of a third pressure differential across the third orifice during the withdrawal of the vaporizable material from the reservoir chamber.

In some embodiments, the first orifice can be configured to direct the flow of vaporizable material from the reservoir chamber to a heating element disposed within a vaporizer body of a vaporizer device. The heating element can be configured to vaporize at least a portion of the vaporizable material into vaporized material when activated. Subsequently, at least a portion of the vaporized material can then enter into and travel along an airflow path of the vaporizer device, a portion of which passes adjacent to the heating element. In other embodiments, the first orifice can be configured to direct the flow of vaporizable material from the reservoir chamber to other areas of the vaporizer cartridge or vaporizer device, such as a wicking element or a secondary reservoir chamber.

The vaporizer device can also include a power source (for example, a battery, which can be a rechargeable battery), and a controller (for example, a processor, circuitry, etc. capable of executing logic) for controlling delivery of heat from the heating element to cause a vaporizable material to be converted from a condensed form (for example, a solid-phase material, such as wax or the like, a liquid, a solution, a suspension, etc.) to the gas phase. The controller can be part of one or more printed circuit boards (PCBs) consistent with certain implementations of the current subject matter.

After conversion of the vaporizable material to the gas phase, at least some of the vaporizable material in the gas phase can condense to form particulate matter in at least a partial local equilibrium with a portion of the vaporizable material that remains in the gas phase. The vaporizable material in the gas phase as well as the condensed phase are part of an aerosol, which can form some or all of an inhalable dose provided by the vaporizer device during a user's puff or draw on the vaporizer device. It should be appreciated that the interplay between the gas phase and condensed phase in an aerosol generated by a vaporizer device can be complex and dynamic, due to factors such as ambient temperature, relative humidity, chemistry, flow conditions in airflow paths (both inside the vaporizer device and in the airways of a human or other animal), and/or mixing of the vaporizable material in the gas phase or in the aerosol phase with other air streams, which can affect one or more physical parameters of an aerosol. In some vaporizer devices, and particularly for vaporizer devices configured for delivery of volatile vaporizable materials, the inhalable dose can exist predominantly in the gas phase (for example, formation of condensed phase particles can be very limited).

The heating element can have a variety of configurations. The heating element can extend from a first surface to a second surface. Non-limiting examples of suitable heating elements include a mesh, a plate, which in certain instances can include at least one groove, or a foil heater, which in certain instances can include at least one tine. Further, the heating element can be configured to be heated using electrical, chemical, or mechanical energy. One type of heating element is a resistive heating element, which can be constructed of, or at least include, a material (e.g., a metal or alloy, such as a nickel-chromium alloy, or a non-metallic resistor) configured to dissipate electrical power in the form of heat when electrical current is passed through one or more resistive segments of the heating element. For example, in one embodiment, a resistive heating element may be embedded on one side of a structure while an opposite side of the structure includes a non-porous ceramic having capillary grooves. In other embodiments, the heating element can be, or include, one or more of a conductive heater, a radiative heater, and a convective heater. For instance, convective heating may be used to deliver heat to at least a portion of the vaporizable material held in an absorbent structure (e.g., a sponge and/or the like) that is disposed downstream (or upstream) from the heating element. Other forms of heating elements are also contemplated herein.

In some embodiments, the heating element can be coupled to a support structure. The support structure can be configured to provide mechanical support to the heating element during and after manufacturing. The support structure can be formed of any suitable material, e.g., one or more polymers, and the like, using any suitable manufacturing method, e.g., additive manufacturing, and the like. The support structure can have a variety of configurations. The support structure can be formed of one or more parts. In some embodiments, the support structure is substantially u-shaped. In other embodiments, the support structure can be sized and shaped differently, including any other possible shape. In one embodiment, the support structure includes a base having two opposing legs extending therefrom. The base and the two opposing legs can have variety of configurations, for example, in some embodiments, the base is substantially rectangular shaped and the two opposing legs have a substantially t-shaped configuration. In other embodiments, the base and/or each of the two opposing legs can be sized and shaped differently, including any other possible shape.

In some embodiments, the support structure can be coupled to the vaporizer body. For example, in some embodiments, the support structure is coupled to a chassis that is configured to house at least a portion of additional components of the vaporizer device such as, for example, a power source, input device(s), sensor(s), output, a controller, communication hardware, memory, and the like. The support structure can be affixed to the vaporizer body.

The heating element can be activated by a variety of mechanisms. The heating element can be activated (e.g., a controller, which is optionally part of the vaporizer body as discussed herein, may cause current to pass from a power source through a circuit including the heating element), in association with a user puffing (i.e., drawing, inhaling, etc.) directly on the vaporizer cartridge itself, or alternatively, on a mouthpiece coupled thereto, to cause air to flow from an air inlet, along a portion of an airflow path that passes adjacent to the heating element. As noted herein, the entrained vaporizable material in the gas phase can condense as it passes through the remainder of the airflow path, which also travels through the interior of the vaporizer cartridge (for example, through one or more internal channels therein), such that an inhalable dose of the vaporizable material in an aerosol form can be delivered from an outlet (for example, in the vaporizer cartridge itself and/or in a mouthpiece coupled thereto) for inhalation by a user. In some embodiments, the vaporizer cartridge includes an internal channel extending through the vaporizer cartridge from an inlet to an outlet of the vaporizer cartridge. In one embodiment, a sidewall of the reservoir chamber can at least partially define a sidewall of the internal channel.

Activation of the heating element can be caused by automatic detection of a puff based on one or more signals generated by one or more sensors. The one or more sensors and the signals generated by the one or more sensors can include one or more of: a pressure sensor or sensors disposed to detect pressure along the airflow path relative to ambient pressure (or optionally to measure changes in absolute pressure), a motion sensor or sensors (for example, an accelerometer) of the vaporizer device, a flow sensor or sensors of the vaporizer device, a capacitive lip sensor of the vaporizer device, detection of interaction of a user with the vaporizer device via one or more input devices (for example, buttons or other tactile control devices of the vaporizer device), receipt of signals from a computing device in communication with the vaporizer device, and/or via other approaches for determining that a puff is occurring or imminent.

As discussed herein, the vaporizer device consistent with implementations of the current subject matter can be configured to connect (such as, for example, wirelessly or via a wired connection) to a computing device (or optionally two or more devices) in communication with the vaporizer device. To this end, the controller can include communication hardware. The controller can also include a memory. The communication hardware can include firmware and/or can be controlled by software for executing one or more cryptographic protocols for the communication.

A computing device can be a component of a vaporizer system that also includes the vaporizer device, and can include its own hardware for communication, which can establish a wireless communication channel with the communication hardware of the vaporizer device. For example, a computing device used as part of a vaporizer system can include a general-purpose computing device (such as a smartphone, a tablet, a personal computer, some other portable device such as a smartwatch, or the like) that executes software to produce a user interface for enabling a user to interact with the vaporizer device. In other implementations of the current subject matter, such a device used as part of a vaporizer system can be a dedicated piece of hardware such as a remote control or other wireless or wired device having one or more physical or soft (i.e., configurable on a screen or other display device and selectable via user interaction with a touch-sensitive screen or some other input device like a mouse, pointer, trackball, cursor buttons, or the like) interface controls.

The vaporizer device can also include one or more outputs or devices for providing information to the user. For example, the outputs can include one or more light emitting diodes (LEDs) configured to provide feedback to a user based on a status and/or mode of operation of the vaporizer device. In some aspects, the one or more outputs can include a plurality of LEDs (i.e., two, three, four, five, or six LEDs). The one or more outputs (i.e., each individual LED) can be configured to display light in one or more colors (for example, white, red, blue, green, yellow, etc.). The one or more outputs can be configured to display different light patterns (for example, by illuminating specific LEDs, varying a light intensity of one or more of the LEDs over time, illuminating one or more LEDs with a different color, and/or the like) to indicate different statuses, modes of operation, and/or the like of the vaporizer device. In some implementations, the one or more outputs can be proximal to and/or at least partially disposed within a bottom end region of the vaporizer device. The vaporizer device may, additionally or alternatively, include externally accessible charging contacts, which can be proximate to and/or at least partially disposed within the bottom end region of the vaporizer device.

In the example in which a computing device provides signals related to activation of a resistive heating element, or in other examples of coupling of a computing device with the vaporizer device for implementation of various control or other functions, the computing device executes one or more computer instruction sets to provide a user interface and underlying data handling. In one example, detection by the computing device of user interaction with one or more user interface elements can cause the computing device to signal the vaporizer device to activate the heating element to reach an operating temperature for creation of an inhalable dose of vapor/aerosol. Other functions of the vaporizer device can be controlled by interaction of a user with a user interface on a computing device in communication with the vaporizer device.

The temperature of a resistive heating element of the vaporizer device can depend on a number of factors, including an amount of electrical power delivered to the resistive heating element and/or a duty cycle at which the electrical power is delivered, conductive heat transfer to other parts of the electronic vaporizer device and/or to the environment, latent heat losses due to vaporization of the vaporizable material from the wicking element, and convective heat losses due to airflow (i.e., air moving across the heating element when a user inhales on the vaporizer device). As noted herein, to reliably activate the heating element or heat the heating element to a desired temperature, the vaporizer device may, in some implementations of the current subject matter, make use of signals from the sensor (for example, a pressure sensor) to determine when a user is inhaling. The sensor can be positioned in the airflow path and/or can be connected (for example, by a passageway or other path) to an airflow path containing an inlet for air to enter the vaporizer device and an outlet via which the user inhales the resulting vapor and/or aerosol such that the sensor experiences changes (for example, pressure changes) concurrently with air passing through the vaporizer device from the air inlet to the air outlet. In some implementations of the current subject matter, the heating element can be activated in association with a user's puff, for example by automatic detection of the puff, or by the sensor detecting a change (such as a pressure change) in the airflow path.

The sensor can be positioned on or coupled to (i.e., electrically or electronically connected, either physically or via a wireless connection) the controller (for example, a printed circuit board assembly or other type of circuit board). To take measurements accurately and maintain durability of the vaporizer device, it can be beneficial to provide a seal resilient enough to separate an airflow path from other parts of the vaporizer device. The seal, which can be a gasket, can be configured to at least partially surround the sensor such that connections of the sensor to the internal circuitry of the vaporizer device are separated from a part of the sensor exposed to the airflow path. The seal can also separate parts of one or more electrical connections between the vaporizer body and the vaporizer cartridge. Such arrangements of the seal in the vaporizer device can be helpful in mitigating against potentially disruptive impacts on vaporizer components resulting from interactions with environmental factors such as water in the vapor or liquid phases, other fluids such as the vaporizable material, etc., and/or to reduce the escape of air from the designated airflow path in the vaporizer device. Unwanted air, liquid or other fluid passing and/or contacting circuitry of the vaporizer device can cause various unwanted effects, such as altered pressure readings, and/or can result in the buildup of unwanted material, such as moisture, excess vaporizable material, etc., in parts of the vaporizer device where they can result in poor pressure signal, degradation of the sensor or other components, and/or a shorter life of the vaporizer device. Leaks in the seal can also result in a user inhaling air that has passed over parts of the vaporizer device containing, or constructed of, materials that may not be desirable to be inhaled.

In some embodiments, the vaporizer cartridge can be selectively coupled to and removable from the vaporizer body using a coupling mechanism. For example, the vaporizer body and the vaporizer cartridge can each include corresponding coupling elements that are configured to releasably engage with each other. That is, in use, once a predetermined length of the vaporizer cartridge is inserted into the vaporizer body, the coupling elements can engage with each other, thereby securing the vaporizer cartridge to the vaporizer body. Likewise, once the vaporizer cartridge needs to be replaced, the coupling element can disengage allowing the vaporizer cartridge to be removed. And subsequently, a new vaporizer cartridge or the refilled vaporizer cartridge can be selectively coupled or recoupled, respectively, to the vaporizer body. Further, the position of the corresponding coupling elements can be dependent at least upon the desired length of vaporizer cartridge to be inserted into the vaporizer body, for example, to avoid the heating element from damage caused by an insertion force.

In one example of coupling elements for coupling the vaporizer cartridge to the vaporizer body, the vaporizer body can include one or more detents (for example, dimples, protrusions, etc.) protruding inwardly from an inner surface of the cartridge receptacle, additional material (such as metal, plastic, etc.) formed to include a portion protruding into the cartridge receptacle, and/or the like. One or more exterior surfaces of the vaporizer cartridge can include corresponding recesses that can fit and/or otherwise snap over such detents or protruding portions when the vaporizer cartridge is inserted into the cartridge receptacle on the vaporizer body. When the vaporizer cartridge and the vaporizer body are coupled (e.g., by insertion of the vaporizer cartridge into the cartridge receptacle of the vaporizer body), the detents or protrusions of the vaporizer body can fit within and/or otherwise be held within the recesses of the vaporizer cartridge, to hold the vaporizer cartridge in place when assembled. Such an assembly can provide enough support to hold the vaporizer cartridge in place, while allowing release of the vaporizer cartridge from the vaporizer body when a user pulls with reasonable force on the vaporizer cartridge to disengage the vaporizer cartridge from the cartridge receptacle. In another embodiments, the exterior surfaces of the vaporizer cartridge can include the one or more detents and the cartridge receptacle can include the one or more recesses.

In some implementations, the vaporizer cartridge, or at least an end the vaporizer cartridge configured for insertion in the cartridge receptacle, can have a non-circular cross section transverse to the axis along which the vaporizer cartridge is inserted into the cartridge receptacle. For example, the non-circular cross section can be approximately rectangular, approximately elliptical (i.e., have an approximately oval shape), non-rectangular but with two sets of parallel or approximately parallel opposing sides (i.e., having a parallelogram-like shape), or other shapes having rotational symmetry of at least order two. In this context, approximate shape indicates that a basic likeness to the described shape is apparent, but that sides of the shape in question need not be completely linear and vertices need not be completely sharp. Rounding of both or either of the edges or the vertices of the cross-sectional shape is contemplated in the description of any non-circular cross section referred to herein.

FIG. 1 illustrates an exemplary vaporizer cartridge 100 for a vaporizer device. More specifically, the vaporizer cartridge 100 includes a reservoir housing 102, a first tubular member 104, and a second tubular member 106. As shown, the vaporizer cartridge 100 is in communication with a heating element 108 of a vaporizer body, like vaporizer body 202 in FIGS. 2-3. Further, the phantom lines shown in FIG. 1 are to illustrate selected portions of the internal structure of the vaporizer cartridge 100. For purposes of simplicity only, certain components of the vaporizer cartridge 100 are not illustrated.

The reservoir housing 102 includes a reservoir chamber 110 that is configured to hold a vaporizable material (not shown). While the reservoir housing 102 can have a variety of sizes and shapes, the reservoir housing 102, as shown in FIG. 1, is substantially rectangular in shape. The reservoir housing 102 includes at least two sets of opposing sidewalls 112, 114 in which the first set of opposing sidewalls 112 extends substantially perpendicular to the second set of opposing sidewalls 114. As shown, these sidewalls 112, 114 define at least a portion of the reservoir chamber 110.

As shown, the first tubular member 104 extends from a first end 104a to a second end 104b, and the second tubular member 106 extends from a third end 106a to fourth end 106b. The first tubular member 104 extends inward from an exterior surface of a first wall 116 of the reservoir housing 102 and into the reservoir chamber 110. As a result, the second end 104b of the first tubular member 104 is positioned within the reservoir chamber 110. Further, the second tubular member 106 extends inward from an exterior surface of a second wall 118 of the reservoir housing 102 and into the reservoir chamber 110. As a result, the fourth end 106b of the second tubular member 106 is positioned within the reservoir chamber 110. In use, when the reservoir chamber 110 is filled with vaporizable material (not shown), the second end 104b of the first tubular member 104 and the fourth end 106b of the second tubular member 106 are each immersed in vaporizable material disposed within the reservoir chamber 110.

In other embodiments, the first end 104a of the first tubular member 104 may be flush (or substantially flush) against the first wall 116 of the reservoir chamber 110. Alternatively, at least a portion of the first tubular member 104 can extend outward from the exterior surface of the first wall 116, thereby resulting in the first end 104a of the first tubular member 104 being positioned at least partially outside of the reservoir housing 102. In other embodiments, the first end 104a of the first tubular member 104 may be recessed within the first wall 116. Nevertheless, it should be appreciated that the length of the first tubular member 104 extending beyond the first wall 116 may be directly proportional to a hydrostatic head pressure within the first tubular member 104. To prevent an unintentional leakage of the vaporizable material due to excessive hydrostatic head pressure within the first tubular member 104, the length of the first tubular member 104 extending beyond the first wall 116 may be proportional to a capillary force resisting the flow of the vaporizable material at the air-liquid interface such that the vaporizable material is not withdrawn from the reservoir chamber 110 unless an inhalation vacuum generates a sufficient pressure differential across the first orifice 120. Alternatively, or in addition, at least a portion of the second tubular member 106 can extend outward from the exterior surface of the second wall 118, thereby resulting in the third end 106a of the second tubular member 106 being positioned completely outside of the reservoir housing 102.

The first tubular member 104 includes the first orifice 120, which extends therethrough such that at least a portion of vaporizable material can be received and directed through the first tubular member 104 to the heating element 108. As discussed above, this occurs in response to an inhalation vacuum that generates a pressure differential across the first orifice 120 that exceeds a first predetermined threshold pressure differential. As such, the inner diameter of the first tubular member 104, and thus, the diameter of the first orifice 120, can control the flow rate of vaporizable material from the reservoir chamber 110. Moreover, as noted, the length of the first tubular member 104 extending beyond the first wall 116 may also control the flow rate of the vaporizable material from the reservoir chamber 110. The capillary force resisting the flow of the vaporizable material at the air-liquid interface may depend at least in part on the diameter of the first tubular member 104. Meanwhile the length of the first tubular member 104 extending beyond the first wall 116 may impact the hydrostatic head pressure of the vaporizable material within the first tubular member 104. Accordingly, the flow rate of the vaporizable material from the reservoir chamber 110 may be controlled by adjusting the diameter of the first tubular member 104 and/or the length of the first tubular member 104 extending beyond the first wall 116. Further, as shown in FIG. 1, the diameter of the first orifice 120 is consistently sized, whereas in other embodiments, the first orifice 120 can have a diameter that exhibits a continuous or discrete variation in size (e.g., two or more sizes) along a length of the first tubular member 104.

The second tubular member 106 includes a second orifice 122 that extends therethrough such that a portion of ambient air outside of the reservoir housing 102 can be received and directed through the second tubular member 106 and into the reservoir chamber 110. As discussed above, this occurs in response to generation of a second pressure differential across the second orifice 122 that exceeds a second predetermined threshold pressure differential during the withdrawal of at least a portion of vaporizable material from the reservoir chamber 110. As such, the inner diameter of the second tubular member 106, and thus the diameter of the second orifice 122, can control the flow rate of ambient air into the reservoir chamber 110. Further, as shown in FIG. 1, the diameter of the second orifice 122 is consistently sized, whereas in other embodiments, the second orifice 122 can have a diameter that varies continuously or discretely in size (e.g., two or more sizes) along a length of the second tubular member 106.

As shown in FIG. 1, the vaporizer cartridge 100 also includes an internal channel 124 that extends from an inlet 126 to an outlet 128 of the vaporizer cartridge 100. The internal channel 124 is configured to direct air and vaporized material through the vaporizer cartridge 100 and exit the outlet 128 for inhalation by a user. While the internal channel 124 can have a variety of configurations, the internal channel 124, as shown in FIG. 1, is defined by two sets of opposing sidewalls 130a, 130b, 132a, 132b. In other embodiments, the internal channel 124 can be sized and shaped differently, including any other possible shape. In use, a user can puff on an end 103 of the vaporizer cartridge 100 such that the air and vaporized material within the vaporizer cartridge 100 can be delivered directly to the user from the outlet 128 for inhalation. Alternatively, a mouthpiece (not shown) can be coupled to the end 103 of the vaporizer cartridge 100, in which case the user can puff on the mouthpiece rather than directly on the end 103 of the vaporizer cartridge 100. As such, the air and vaporized material within the vaporizer cartridge 100 can travel from the outlet 128 into the mouthpiece for inhalation by the user.

Figure 2:
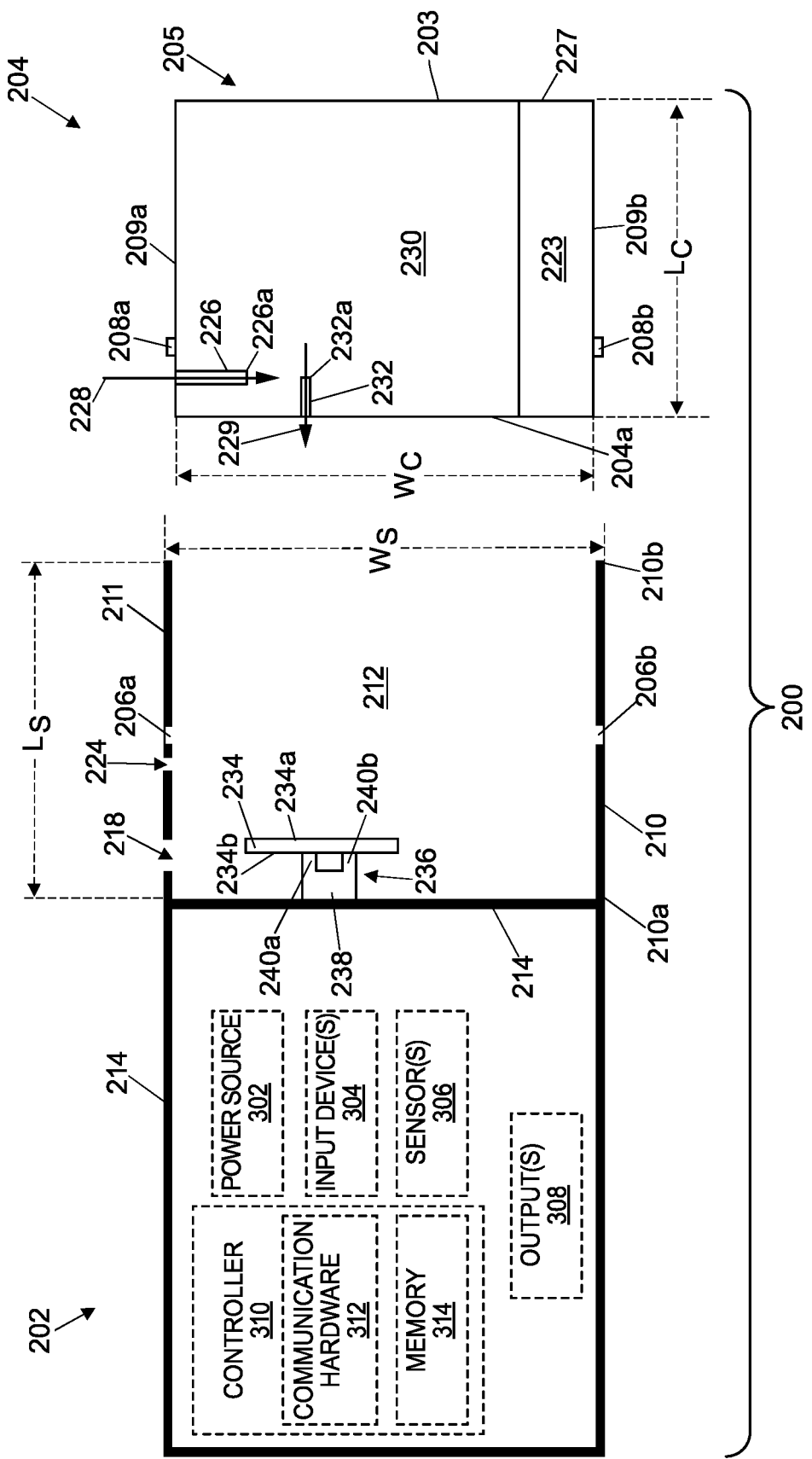
FIG. 2 is a partially transparent, front view of an embodiment of a vaporizer device that includes a vaporizer cartridge and a vaporizer body having a heating element disposed therein, showing the vaporizer cartridge and the vaporizer body separated from each other.
Figure 3:
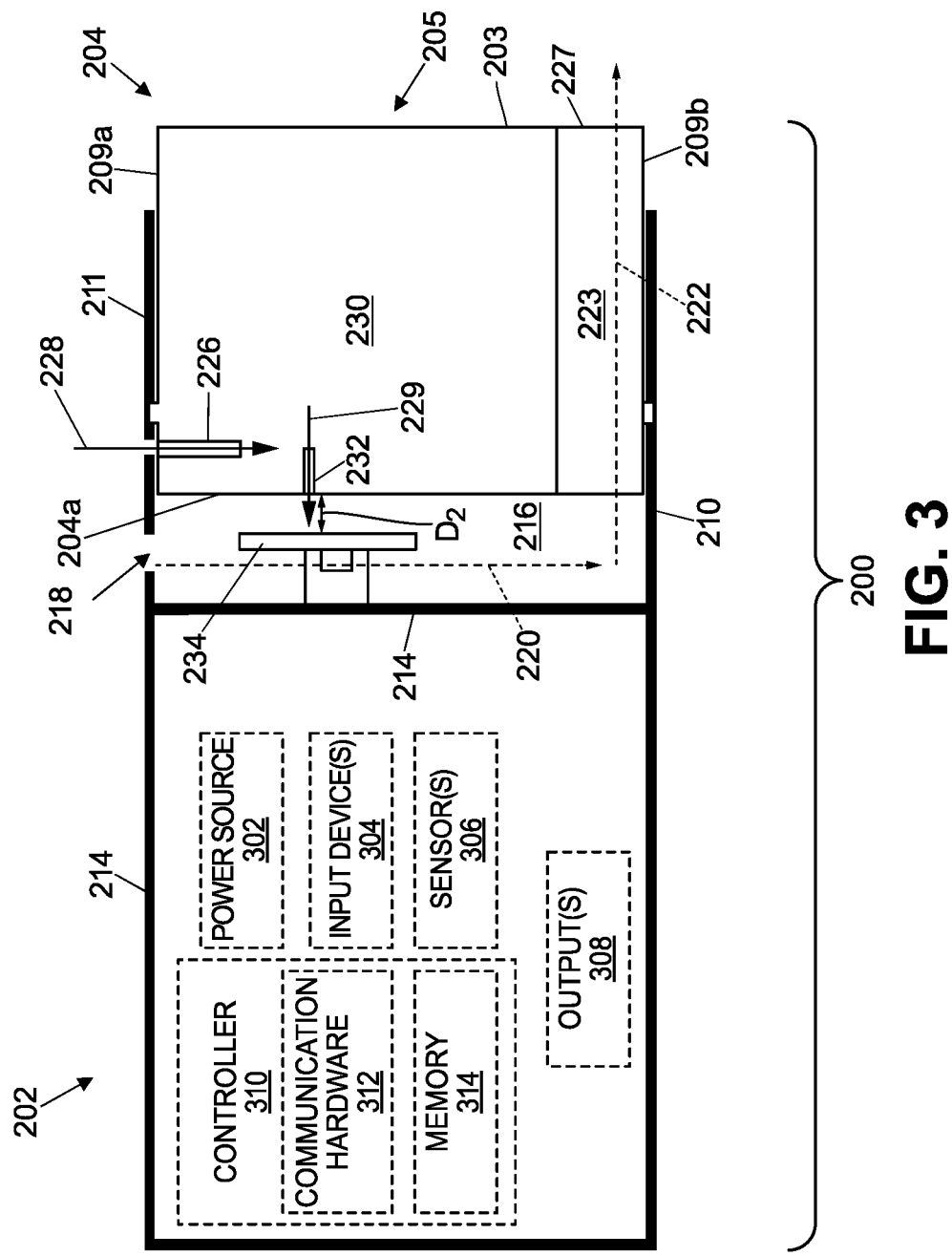
FIG. 3 is a partially transparent, front view of the vaporizer device of FIG. 2, showing the vaporizer cartridge inserted into a cartridge receptacle of the vaporizer body.

Further, as shown in FIG. 1, the vaporizer cartridge 100 also includes a first set of coupling elements 134a. 134b that can be used to selectively couple the vaporizer cartridge 100 to a vaporizer body, such as vaporizer body 202 in FIGS. 2-3. While the first set of coupling elements can have a variety of configurations, the first set of coupling elements 134a, 134b, as shown in FIG. 1, include two protrusions extending outwardly from two opposing sidewalls of the vaporizer cartridge 100.

FIGS. 2-3 illustrate an exemplary vaporizer device 200 that includes a vaporizer body 202 and a vaporizer cartridge 204. In FIG. 2, the vaporizer body 202 and the vaporizer cartridge 204 are illustrated in a decoupled configuration, whereas in FIG. 3, the vaporizer body 202 and the vaporizer cartridge 204 are illustrated in a coupled configuration. The vaporizer cartridge 204 is similar to vaporizer cartridge 100 in FIG. 1 and therefore similar components are not described in detail herein.

The vaporizer body 202 and the vaporizer cartridge 204 can be coupled to each other by way of corresponding coupling elements. For example, as shown in FIGS. 2-3, the vaporizer body 202 includes a first set of coupling elements 206a, 206b, and the vaporizer cartridge 204 includes a second set of corresponding coupling elements 208a, 208b. While the first and second set of coupling elements can have a variety of configurations, in this illustrated embodiment, the first set of coupling elements 206a, 206b include two recess channels extending inward into the vaporizer body 202 and the second set of coupling elements 208a, 208b include two protrusions extending outwardly from two opposing sidewalls 209a, 209b of the vaporizer cartridge 204.

The vaporizer body 202 can have a variety of configurations. As shown in FIGS. 2-3, the vaporizer body 202 includes a sleeve 210 that extends from a distal end 210a to a proximal end 210b. The sleeve 210 defines a cartridge receptacle 212 within the vaporizer body 202 that is configured to receive at least a portion of the vaporizer cartridge 204. The distal end 210a of the sleeve 210 is coupled to a chassis 214 that is configured to house at least a portion of additional components of the vaporizer device 200, such as, for example, any of the components discussed above (e.g., a power source, input device(s), sensor(s), output, a controller, communication hardware, memory, and the like). In this illustrated embodiment, the vaporizer device 200 includes a power source 302, input device(s) 304, sensor(s) 306, output 308, a controller 310, communication hardware 312, memory 314, which, as shown in FIGS. 2-3, are disposed within the vaporizer body 202. Once the vaporizer cartridge 204 is coupled to the vaporizer body 202, a vaporization chamber 216, as shown in FIG. 3, is created within the cartridge receptacle 212 between the chassis 214 and a distal surface 204a of the vaporizer cartridge 204.

Further, as shown in FIGS. 2-3, a first air inlet 218 extends through a wall 211 of the sleeve 210. This first air inlet 218 is configured to allow at least a portion of ambient air outside of the vaporizer body 202, and thus outside of the reservoir housing 205 of the vaporizer cartridge 204, to enter the vaporizer device 200. In use, when a user puffs directly on an end 203 of the vaporizer cartridge 204, at least a portion of ambient air enters the vaporizer body 202 and travels through a first airflow path 220 of the vaporization chamber 216. Alternatively, a mouthpiece (not shown) can be coupled to the end 203 of the vaporizer cartridge 204, in which case the user can puff on the mouthpiece rather than directly on the end 203 of the vaporizer cartridge 204. As described in more detail below, vaporized material joins the first airflow path 220 and combines with at least a portion of the air within the vaporization chamber 216 to form a mixture. The mixture travels through the remaining portion of the first airflow path 220 and then through a second airflow path 222 that extends through an internal channel 223 of the vaporizer cartridge 204. As such, the first and second airflow paths 220, 222 are in fluid communication with each other.

Further, a second air inlet 224 extends through the wall 211 of the sleeve 210. As shown in FIGS. 2-3, this second air inlet 224 is in fluid communication with a second orifice (obscured), like second orifice 122 in FIG. 1. The second orifice extends through a second tubular member 226 of the vaporizer cartridge 204. As shown, the first and second air inlets 218, 224 are in fluid communication with each other. As a result, the second orifice is in fluid communication with ambient air outside of the vaporizer device 200, and thus outside of the reservoir housing 205, such that a portion of the ambient air (illustrated as arrow 228) can be received within the second orifice. Further, one end 226a of the second tubular member 226, and thus one end of the second orifice, is positioned within a reservoir chamber 230 of the reservoir housing 205, and therefore, the second orifice is also in fluid communication with the reservoir chamber 230.

As described above, the second tubular member 226, and thus the second orifice, directs the ambient air 228 into a reservoir chamber 230 of the vaporizer cartridge 204 while at least a portion of vaporizable material (illustrated as arrow: 229) is being withdrawn through a first orifice (obscured), like first orifice 120 in FIG. 1. The first orifice extends through a first tubular member 232 of the vaporizer cartridge 204. As shown, one end 232a of the first tubular member 232, and thus one end of the first orifice, is positioned within the reservoir chamber 230). As a result, the first orifice is in fluid communication with reservoir chamber 230. As further shown, the first tubular member 232, and thus the first orifice, directs the at least a portion of vaporizable material 229 towards a heating element 234 of the vaporizer body 202.

As shown in FIG. 2, the heating element 234 is disposed within the cartridge receptacle 212. Further, as shown in FIG. 3, the heating element 234 ultimately resides within the vaporization chamber 216 when the vaporizer body 202 and vaporizer cartridge 204 are coupled together. While the heating element 234 can have variety of configurations, the heating element, as shown in FIGS. 2-3, includes a mesh that extends from a first surface 234a to a second surface 234b. Alternate embodiments of the heating element 234 may include a resistive heating element (coupled with a non-porous ceramic having capillary grooves) or a convective heating element configured to deliver heat upstream or downstream to at least a portion of the vaporizable material 229 held in an absorbent structure (e.g., a sponge and/or the like). Further, one or more electrical contacts (not shown) can be attached to the mesh so as to operatively couple the mesh, and thus the heating element 234, to at least the power source 302 disposed within the vaporizer body 202. The one or more electrical contacts can have a variety of configurations. For example, in one embodiment, the one or more electrical contacts can be in the form of wires.

As shown, the second surface 234b of the mesh is coupled to a support structure 236. In this illustrated embodiment, the support structure 236 includes a base 238 and first and second opposing legs 240a. 240b extending outwardly from the base 238 and spaced apart relative to each other at a distance. While the base 238 can have a variety of configurations, the base 238, as shown in FIGS. 2-3, is substantially rectangular in shape. In other embodiments, the base 238 can be sized and shaped differently, including any other possible shape. While the first and second opposing legs 240a, 240b can have a variety of configuration, each of the first and second opposing legs 240a, 240b can have a substantially t-shaped configuration. Further, as shown, the first and second opposing legs 240a, 240b are sized and shaped the same. In other embodiments, the first and second opposing legs 240a. 240b can be sized and shaped differently relative to each other, including any other possible shape. As shown, the base 238 and the first and second opposing legs 240a, 240b are integrally formed.

In use, once the vaporizer cartridge 204 is coupled to the vaporizer body 202, a vacuum (e.g., an inhalation vacuum) can be generated within the vaporizer device 200 by a user puffing on the end 203 of the vaporizer cartridge 204. As the user puffs on the vaporizer cartridge 204, the vacuum increases, and can ultimately exceed a predetermined threshold vacuum. Once the vacuum exceeds the predetermined threshold vacuum (e.g., a predetermined threshold inhalation vacuum), at least a portion of the vaporizable material 229 is drawn along the first orifice of the first tubular member 232 from the reservoir chamber 230 and into the vaporization chamber 216. As a result of the vaporizable material 229 being drawn from the reservoir chamber 230, the internal pressure of the reservoir chamber 230 decreases. That is, as the vacuum exceeds the predetermined threshold vacuum, an effective pressure differential across the first orifice is created to allow the flow of at least a portion of vaporizable material 229 from the reservoir chamber 230 and through the first orifice for vaporization (e.g., into the vaporization chamber 216).

As mentioned above, a flow regulator valve can be implemented within the vaporizer device 200 and positioned upstream of the first tubular member 232. For example, in one embodiment, the flow regulator valve can be formed of a resilient member that defines a portion of the wall 211 of the sleeve 210. The flow regulator valve can be configured to allow at least a portion of ambient air outside of the vaporizer body 202 to enter into the vaporizer device 200 over a first range of inhalation vacuums that are greater than predetermined threshold vacuum. Further, the flow regulator valve can be configured to prevent ambient air from entering the vaporizer device 200 over a second range of inhalation vacuums that is greater than the first range of inhalation vacuums. In this way, during use, once the predetermined threshold vacuum is reached, a substantially consistent pressure drop across the first orifice of the first tubular member 232 can be maintained over the first and second ranges of inhalation vacuums, and thus over varying inhalation vacuums that fall within such ranges.

While the vaporization material is being withdrawn from the reservoir chamber 230, a portion of ambient air 228 outside of the reservoir housing 205 is also drawn along the second orifice of the second tubular member 226 and into the reservoir chamber 230. As a result, the internal pressure of the reservoir chamber 230 begins to increase. That is, as the vacuum exceeds the predetermined threshold vacuum, an effective pressure differential across the second orifice is created to allow the flow of at least a portion of ambient air 228 through the second orifice and into the reservoir chamber 230. This influx of ambient air 228 into the reservoir chamber 230 replaces at least a portion of the volume of the vaporizable material being withdrawn therefrom. As a result, the internal pressure of the reservoir chamber 230) can at least be partially equalized, for example, with an ambient pressure. Otherwise, without a mechanism to equalize the internal pressure of the reservoir chamber 230, negative pressure (and potentially a vacuum) can develop within the reservoir chamber 230 due to the withdrawal of the vaporizable material. This negative pressure (or vacuum) can hinder withdraw of the vaporizable material from the reservoir chamber 230 including by increasing the threshold vacuum required to overcome the negative pressure in the reservoir chamber 230) and withdraw additional vaporizable material from the reservoir chamber 230).

Further, the heating element 234 is also activated by the user puffing on the end 203 of the vaporizer cartridge 204 and at least a portion of vaporizable material 229 drawn along the first orifice and into the vaporization chamber 216 is vaporized into vaporized material. This puffing also concurrently draws ambient air into the vaporization chamber 216 of the vaporizer body 202 through the first air inlet 218 of the sleeve 210. As a result, at least a portion of the vaporized material joins the air traveling along the first airflow path 220. Subsequently, at least a portion of the joined vaporized material and air continues to travel through the vaporizer body 202 and into the second airflow path 222 of the vaporizer cartridge 204. As the joined vaporized material and air travel through at least the second airflow path 222, and thus, the internal channel 223 of the vaporizer cartridge 204, they at least partially condense into aerosol for subsequent inhalation by a user.

Figure 4:
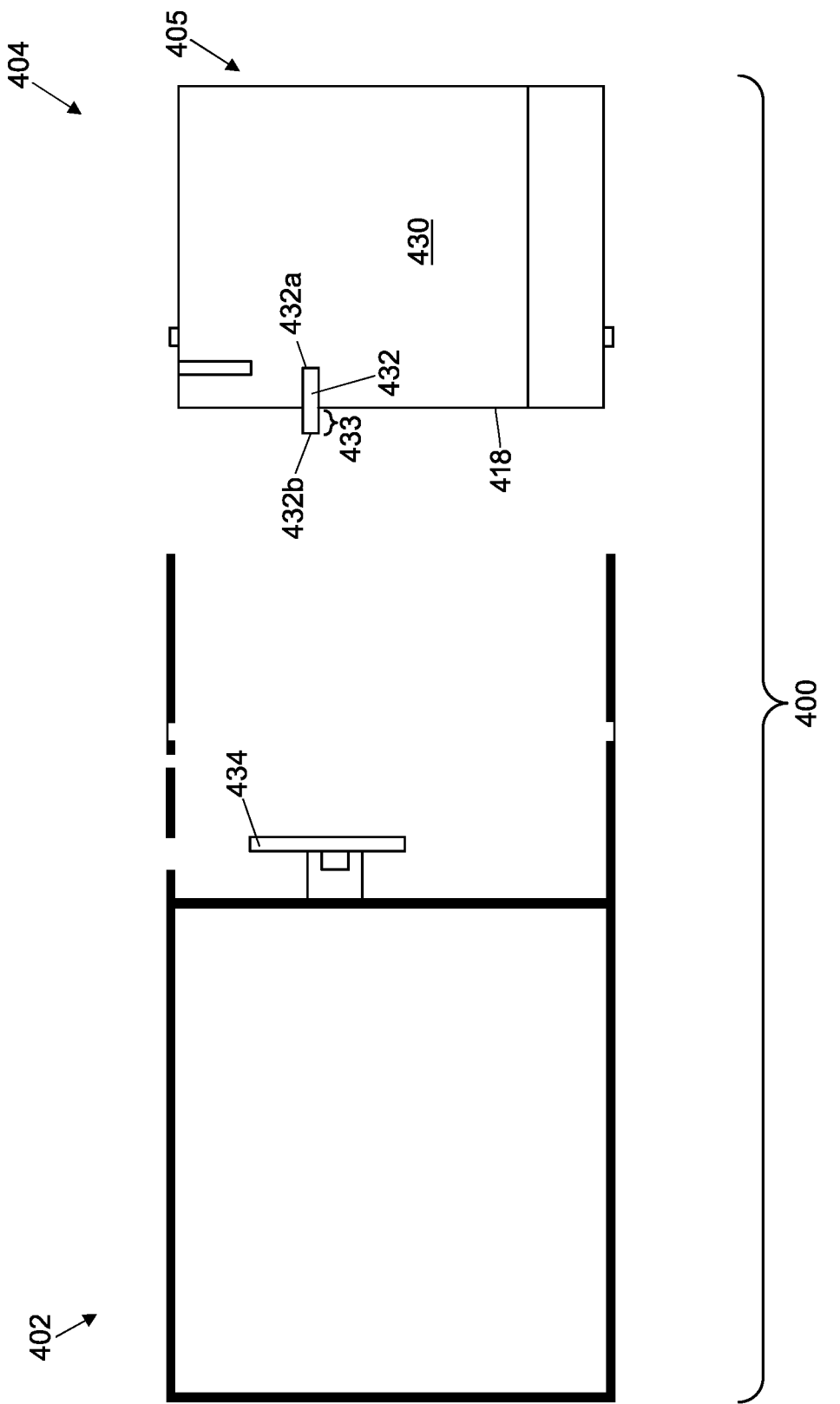
FIG. 4 is a partially transparent, front view of another embodiment of a vaporizer device that includes a vaporizer cartridge and a vaporizer body having a heating element disposed therein.
Figure 5:
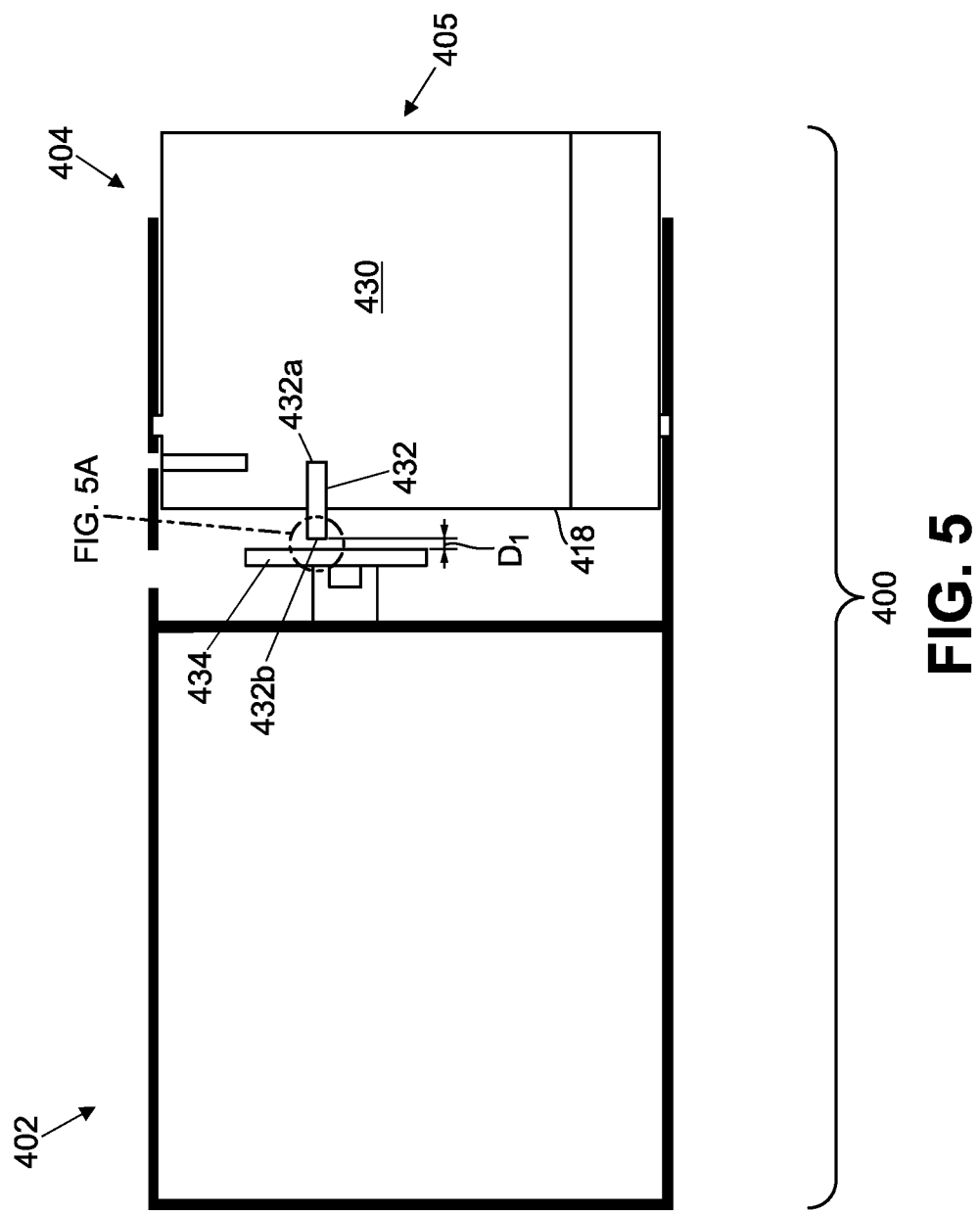
FIG. 5 is a partially transparent, front view of the vaporizer device of FIG. 4, showing the vaporizer cartridge inserted into a cartridge receptacle of the vaporizer body.

FIGS. 4 and 5 illustrate an exemplary vaporizer device 400 that includes a vaporizer body 402 and a vaporizer cartridge 404. In FIG. 4, the vaporizer body 402 and the vaporizer cartridge 404 are illustrated in a decoupled configuration, whereas in FIG. 5, the vaporizer body 402 and the vaporizer cartridge 404 are illustrated in a coupled configuration. The vaporizer body 402 and the vaporizer cartridge 404 are similar to vaporizer body 202 and vaporizer cartridge 204 in FIGS. 2-3 and therefore similar components thereof are not described in detail herein. In this illustrated embodiment, however, a portion 433 of the first tubular member 432 extends outward from the second wall 418 of the reservoir housing 405.

Figure 5A:
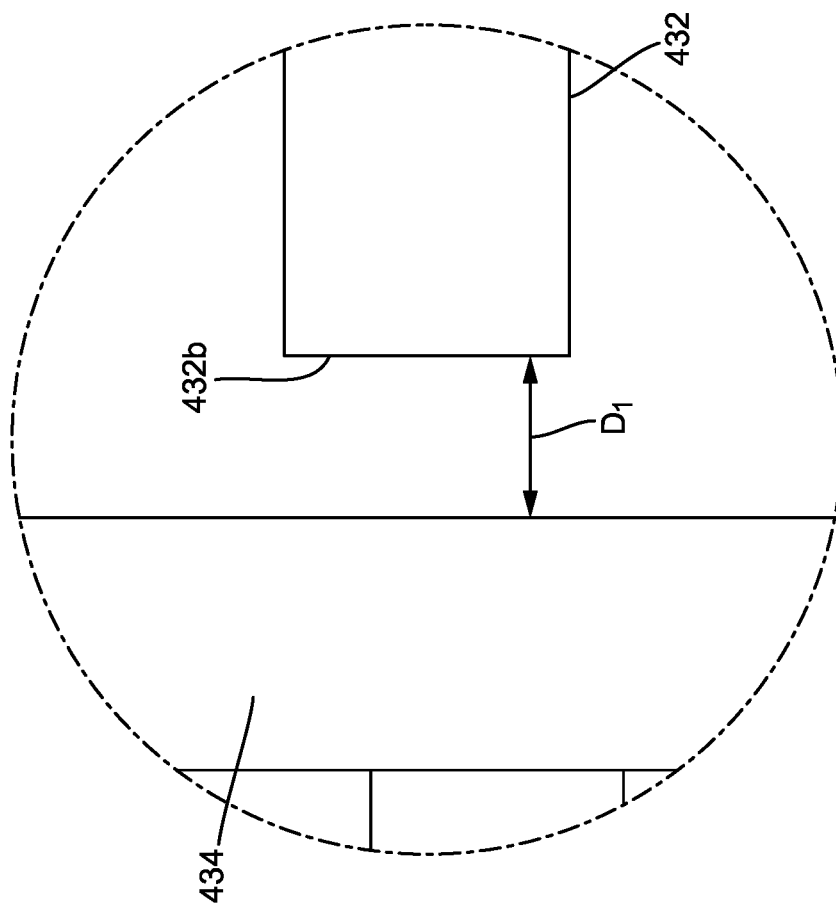
FIG. 5A is a magnified view of a portion of the vaporizer device of FIG. 5.

As shown, a first end 432a of the first tubular member 432, and thus one end of the first orifice (obscured), like first orifice 120 in FIG. 1, extending through the first tubular member 432, is positioned within the reservoir chamber 430, and a second, opposing end 432b of the first tubular member 432, and thus another, opposing end of the first orifice, is positioned completely outside of the reservoir housing 405. As a result, when the vaporizer body 402 and the vaporizer cartridge 404 are in a coupled configuration, as shown in FIG. 5, and in more detail in FIG. 5A, the second end 432b of the first tubular member 432 is positioned at a first distance ($D_1$) relative to the heating element 434. This first distance ($D_1$) is less than a second distance ($D_2$) between the first tubular member 232 and the heating element 234 of the vaporizer device 200 in FIGS. 2-3. In this way, the vaporizable material can be directed in a more control manner to the heating element 434.

Terminology

For purposes of describing and defining the present teachings, it is noted that unless indicated otherwise, the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" are intended to include the plural forms as well, unless the context clearly indicates otherwise. It will be further understood that the terms "comprises" and/or "comprising." when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B:" "one or more of A and B:" and "A and/or B" are each intended to mean "A alone, B alone, or A and B together." A similar interpretation is also intended for lists including three or more items. For example, the phrases "at least one of A, B, and C:" "one or more of A, B, and C:" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The disclosed subject matter has been provided here with reference to one or more features or embodiments. Those skilled in the art will recognize and appreciate that, despite of the detailed nature of the exemplary embodiments provided here, changes and modifications may be applied to said embodiments without limiting or departing from the generally intended scope. These and various other adaptations and combinations of the embodiments provided here are within the scope of the disclosed subject matter as defined by the disclosed elements and features and their full set of equivalents.

What is claimed is:

1. A cartridge for a vaporizer device, the cartridge comprising:
    a reservoir housing including a reservoir chamber configured to contain a vaporizable material;
    a first orifice extending through a first wall of the reservoir housing and in fluid communication with the reservoir chamber, the first orifice being configured to allow at least a portion of the vaporizable material to be withdrawn from the reservoir chamber in response to generation of a first pressure differential across the first orifice that exceeds a first predetermined threshold pressure differential; and
    a second orifice extending through a second wall of the reservoir housing and in fluid communication with the reservoir chamber, the second orifice being configured to allow a portion of ambient air that is outside the reservoir housing to enter the reservoir chamber in response to generation of a second pressure differential across the second orifice that exceeds a second predetermined threshold pressure differential during the withdrawal of the vaporizable material from the reservoir chamber.

2. The cartridge of claim 1, wherein the first orifice is configured to control a flow rate of the vaporizable material being withdrawn from the reservoir chamber along the first orifice.

3. The cartridge of claim 1, wherein the second orifice is configured to control a flow rate of the ambient air being drawn along the second orifice into the reservoir chamber.

4. The cartridge of claim 1, wherein the vaporizable material is maintained within the reservoir chamber until the first pressure differential exceeds the first predetermined threshold pressure differential.

5. The cartridge of claim 1, wherein the first pressure differential exceeds the first predetermined threshold pressure differential in response to the first orifice being exposed to an inhalation vacuum that exceeds a predetermined threshold inhalation vacuum.

6. The cartridge of claim 1, wherein the first orifice has a first diameter and the second orifice has a second diameter that is greater than the first diameter.

7. The cartridge of claim 1, further comprising a first tubular member that extends through the first wall of the reservoir housing and into the reservoir chamber, wherein the first tubular member defines the first orifice.

8. The cartridge of claim 1, further comprising a second tubular member that extends through the second wall of the reservoir housing and into the reservoir chamber, wherein the second tubular member defines the second orifice.

9. The cartridge of claim 1, wherein the first orifice is configured to direct the vaporizable material being withdrawn from the reservoir chamber along the first orifice to a heating element for vaporization.

10. The cartridge of claim 1, further comprising a third orifice extending through the first wall of the reservoir housing and in fluid communication with reservoir chamber, wherein the third orifice is configured to allow at least another portion of the vaporizable material to be withdrawn from the reservoir chamber in response to generation of a third pressure differential across the third orifice that exceeds a third predetermined threshold pressure differential.

11. The cartridge of claim 1, further comprising a third orifice extending through the second wall of the reservoir housing and in fluid communication with reservoir chamber, wherein the third orifice is configured to allow at least another portion of ambient air outside of the reservoir housing to enter the reservoir chamber in response to generation of a third pressure differential across the third orifice that exceeds a third predetermined threshold pressure differential during the withdrawal of the vaporizable material from the reservoir chamber.

12. A cartridge for a vaporizer device, the cartridge comprising:
    a reservoir housing including a reservoir chamber configured to contain a vaporizable material; and
    first and second tubular members that are each in fluid communication with and at least partially extending into the reservoir chamber,
    wherein the first tubular member is configured to withdraw at least a portion of the vaporizable material from the reservoir chamber in response to being exposed to an inhalation vacuum that exceeds a predetermined threshold inhalation vacuum, and
    wherein the second tubular member is configured to concurrently allow a portion of ambient air outside of the reservoir housing to pass therethrough and into the reservoir chamber while the inhalation vacuum is above the predetermined threshold inhalation vacuum.

13. The cartridge of claim 12, wherein the first tubular member has a first inner diameter and the second tubular member has a second inner diameter that is greater than the first inner diameter.

14. The cartridge of claim 12, further comprising a third tubular member that is in fluid communication with and at least partially extending into the reservoir chamber, wherein the third tubular member is configured to withdraw at least another portion of the vaporizable material from the reservoir chamber in response to being exposed to the inhalation vacuum that exceeds the predetermined threshold inhalation vacuum.

15. The cartridge of claim 12, further comprising a third tubular member that is in fluid communication with and at least partially extending into the reservoir chamber, wherein the third tubular member is configured to concurrently allow at least another portion of ambient air outside the reservoir housing to pass therethrough and into the reservoir chamber while the inhalation vacuum is above the predetermined threshold inhalation vacuum.

16. A vaporizer device, comprising:
- a vaporizer body that includes a heating element disposed therein; and
- a cartridge that is selectively coupled to and removable from the vaporizer body, the cartridge including:
  - a reservoir housing including a reservoir chamber configured to contain a vaporizable material,
  - a first orifice extending through a first wall of the reservoir housing and in fluid communication with the reservoir chamber, the first orifice being configured to allow at least a portion of the vaporizable material to be withdrawn from the reservoir chamber in response to generation of a first pressure differential across the first orifice that exceeds a first predetermined threshold pressure differential, and
  - a second orifice extending through a second wall of the reservoir housing and in fluid communication with the reservoir chamber, the second orifice being configured to allow a portion of ambient air that is outside the reservoir housing to enter the reservoir chamber in response to generation of a second pressure differential across the second orifice that exceeds a second predetermined threshold pressure differential during the withdrawal of the vaporizable material from the reservoir chamber;
- wherein the first orifice is in communication with the heating element for vaporization of the withdrawn vaporizable material into a vaporized material.

17. The vaporizer device of claim 16, wherein the vaporizer body includes a first airflow path and the cartridge includes a second airflow path that is in fluid communication with the first airflow path.

18. The vaporizer device of claim 17, wherein the vaporizer body includes at least one inlet that is configured to substantially allow airflow to pass into the vaporizer body, and wherein the at least one inlet is in fluid communication with the first airflow path.

19. A vaporizer device, comprising:
- a vaporizer body that includes a heating element disposed therein; and
- a cartridge that is selectively coupled to and removable from the vaporizer body, the cartridge including:
  - a reservoir housing including a reservoir chamber configured to contain a vaporizable material,
  - a first orifice extending through a first wall of the reservoir housing and in fluid communication with the reservoir chamber, the first orifice being configured to allow at least a portion of the vaporizable material to be withdrawn from the reservoir chamber in response to generation of a first pressure differential across the first orifice that exceeds a first predetermined threshold pressure differential, and
  - a second orifice extending through a second wall of the reservoir housing and in fluid communication with the reservoir chamber, the second orifice being configured to allow a portion of ambient air that is outside the reservoir housing to enter the reservoir chamber in response to generation of a second pressure differential across the second orifice that exceeds a second predetermined threshold pressure differential during the withdrawal of the vaporizable material from the reservoir chamber;
- wherein the first orifice is in communication with the heating element for vaporization of the withdrawn vaporizable material into a vaporized material and wherein the heating element is downstream of the cartridge.

\* \* \* \* \*